United States Patent
Haenel et al.

(10) Patent No.: US 6,290,926 B1
(45) Date of Patent: Sep. 18, 2001

(54) CATALYSTS MADE FROM TRANSITION METAL COMPOUNDS AND 4, 5-DIPHOSPHINOACRIDINE-LIGANDS

(75) Inventors: Matthias W. Haenel; Stefan Hillebrand, both of Mülheim an der Ruhr (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 09/331,274

(22) PCT Filed: Dec. 9, 1997

(86) PCT No.: PCT/EP97/06866

§ 371 Date: Jun. 17, 1999

§ 102(e) Date: Jun. 17, 1999

(87) PCT Pub. No.: WO98/27101

PCT Pub. Date: Jun. 25, 1998

(30) Foreign Application Priority Data

Dec. 17, 1996 (DE) ............................................ 196 52 350

(51) Int. Cl.$^7$ ................ C01B 31/20; C07F 9/50
(52) U.S. Cl. ................ 423/437.2; 423/655; 423/659; 546/23
(58) Field of Search ................ 423/655, 437.2, 423/659; 546/23

(56) References Cited

PUBLICATIONS

Hermann A. Mayer, "Stereochemical control of transition metal complexes by polyphosphine ligands", Chemical Reviews, Bd. 94, Nr. 5, 1994, pp. 1239–1272.

H. Schmid, "Uber die Einwirkung von N–Brom–succinimid auf Acridin" Helvetica Chimica Acta., Bd. XXX, Nr. VII, 1947, pp. 1965–1975.

Adriano Sacco, Synthesis and structures of . . . Pt(II), Journal of Organometallic Chemistry, Bd. 356, Nr. 3, 1988, pp. 397–409.

Guoxin Zhu:, "Asymmetric allylicylkylation cotalyzed by Pd complexes with new chiral ligands", Tetrahedron Letters, Bd. 37, Nr. 26, Jun. 24, 1996, pp. 4475–4478.

*Primary Examiner*—Stuart L. Hendrickson
(74) *Attorney, Agent, or Firm*—Norris McLaughlin & Marcus

(57) ABSTRACT

The present invention relates to the preparation of novel catalysts made from transition metal compounds and "tridentate" 4,5-diphosphinoacridine ligands ("acriphos"). The novel ligands employed herein are diphosphine compounds of 4,5-disubstituted acridine which coordinate transition metals in a three-fold way with the two phosphorus atoms and the acridine nitrogen. The invention also relates to the use of the novel catalysts for the catalysis of carbon monoxide conversion via the water-gas shift reaction (WGSR: $CO+H_2O \rightarrow CO_2+H_2$) and for the catalysis of the following reactions: hydroformylation, carbonylation, carboxylation, hydrogenation, hydrocyanogenation, hydrosilylation, polymerization, isomerization, cross-couplings and metathesis. The invention further relates to heretofore unknown syntheses of the 4,5-diphosphinoacridines through the reaction of 4,5-difluoroacridine with alkali metal phosphides $[R_2P^-M^+(M^+=Li^+, Na^+, K^+, Rb^+, Cs^+,$ preferably $K^+)]$ or through the reaction of 4,5-dibromoacridine with chlorophosphines ($R_2PCl$) and magnesium, and to the preparation of 4,5-difluoroacridine and 4,5-dibromoacridine.

36 Claims, No Drawings

CATALYSTS MADE FROM TRANSITION METAL COMPOUNDS AND 4,5-DIPHOSPHINOACRIDINE-LIGANDS

This application is a 371 of PCT/FP97/06866, which was filed on Dec. 9, 1997.

The present invention relates to the preparation of novel catalysts made from transition metal compounds and 4,5-diphosphinoacridine ligands ("acriphos"). The novel ligands employed herein are diphosphine compounds of 4,5-disubstituted acridine of general formula (I) which coordinate transition metals with the two phosphorus atoms and the acridine nitrogen to form transition metal complexes of general formula (II):

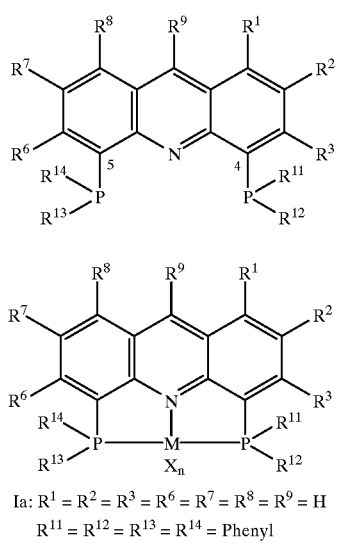

Ia: $R^1 = R^2 = R^3 = R^6 = R^7 = R^8 = R^9 = H$
$R^{11} = R^{12} = R^{13} = R^{14} = Phenyl$ The transition metal complexes (II) are novel catalyst systems which can be employed in the catalysis of numerous chemical reactions.

Catalyst systems made from transition metal compounds and phosphine ligands are known in homogeneous catalysis. In the past, a wide variety of monophosphine and "bidentate" diphosphine compounds have been synthesized, and their application in homogeneous catalysis examined [F. R. Hartley and S. Patai (editors), *The Chemistry of Organophosphorus Compounds*, Vol. 1, Wiley, New York, 1990; L. H. Pignolet (editor), Homogeneous *Catalysis with Metal Phosphine Complexes*, Plenum Press, New York, 1983]. Both monophosphine and diphosphine ligands in divalent nickel, palladium and platinum compounds as well as in complex compounds with other transition metals have the disadvantage of becoming oxidized to phosphine oxides in a redox reaction with the transition metal in the presence of water [P. Giannoccaro, E. Panncciulli and G. Vasapallo, *Inorg. Chim. Acta* 96 (1985) 179; P. Giannoccaro und G. Vasapallo, *Inorg. Chim. Acta* 72 (1983) 51]. In such cases, since the phosphine ligand is irreversibly consumed, the catalysis either is completely brought to a standstill or, in the most favorable case, can be maintained by employing the ligands in a large excess from the beginning or replenishing them in the course of catalysis. Further strengthening of the transition metal-ligand bond can be achieved with "tridentate" triphosphine or "tridentate" diphosphine ligands having a third coordination site with another donor atom, so that their phosphorus centers are less susceptible to chemical changes. However, in contrast to mono- and diphosphines, "tridentate" ligands have found little use for catalysts. In a new review article on polyphosphine ligands [H. A. Mayer and W. C. Kaska, *Chem. Rev.* 94 (1994) 1239–1272], the authors have written: "Thus, the idea to use polyphosphine-stabilized metal complexes as catalysts has emerged early. However, the non-dissociative character of the chelating polyphosphines is a disadvantage in catalytic processes which require open sites at the metal center. This seems to limit the application of polyphosphines in catalysis to processes which do not need many available positions at the metal center" (quotation on page 1266).

The "tridentate" ligand 2,6-bis(diphenylphosphinomethyl)pyridine (III, R=Ph) has been known for a long time [W. V. Dahlhoff and S. M. Nelson, *J. Chem. Soc. A* 1971, 2184; G. Vasapollo, P. Giannoccaro, C. F. Nobile und A. Sacco, *Inorg. Chim. Acta* 48 (1981) 125; A. Sacco, P. Giannoccaro and G. Vasapollo, *Inorg. Chim. Acta* 83 (1984) 125; G. Vasapollo, C. F. Nobile and A. Sacco,. *J. Organomet. Chem.* 296 (1985) 435; Q. Jiang, D. Van Plew, S. Murtuza, and X. Zhang, *Tetrahedron Lett.* 37 (1996) 797]. Ligand (III) has different properties from those of ligands (I) and has some disadvantages with respect to the latter. In addition to metal complexes of structure (IV) with three-coordination in a "T"-shaped planar arrangement similar to that in (II), complexes of structure (V) are also known wherein the diphosphine compounds (III) only serve the function of "bidentate" ligands without an additional metal-nitrogen coordination [P. Giannoccaro, G. Vasapollo and A. Sacco, *J. Chem. Soc. Chem. Commun.* 1980, 1136]. One severe drawback of ligand (III) is that basic reagents, such as alcoholates, cleave one of the reactive benzylic hydrogens in transition metal complexes (IV) as a proton, resulting in the formation of "phosphinomethanide" structures (VI) with C—P double bond character. Thus, catalyst systems with (III) as ligands cannot be used in the presence of basic and highly nucleophilic reagents on principle. In addition, ligand (III), being a benzylic phosphine, is extremely sensitive to oxygen [A. Sacco, G. Vasapollo, C. F. Nobile, A. Piergiovanni, M. A. Pellinghelli and M. Lafranchi,. *J. Organomet. Chem.* 356 (1988) 397].

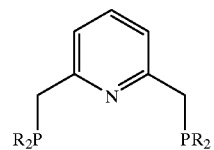

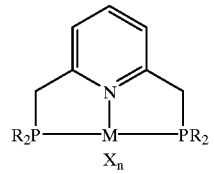

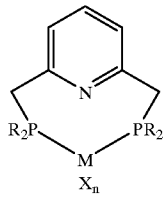

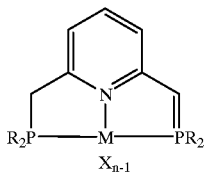

VI

Surprisingly, it has now been found that novel transition metal complex compounds (II) prepared from the novel 4,5-diphosphinoacridine ligands (I, "acriphos") and transition metal compounds of different oxidation stages, wherein $R^1$, $R^2$, $R^3$, $R^6$, $R^7$, $R^8$ and $R^9$ represent hydrogens or, preferably $R^9$ or $R^2$ and $R^7$, represent one or two alkyl or alkoxy groups each having from 1 to 12 carbon atoms or aryl, $NH_2$, $NR_2$, $NR_3^+Y^-$ ($R=C_1$ to $C_4$ alkyl, $Y^-$=anions such as halides), OH, COOH, $SO_3H$, halogens or $CF_3$, or wherein $R^1$, $R^2$, $R^3$, $R^6$, $R^7$, $R^8$ and $R^9$ =H or, preferably $R^9$ or $R^2$ and $R^7$, represent one or two alkyl, alkoxy or aryl groups substituted with groups such as $NH_2$, $NR_2$, $NR_3^+Y^-$ ($R=C_1$ to $C_4$ alkyl, $Y^-$=anions such as halides), OH, COOH, $SO_3H$, halogens or $CF_3$, wherein $R^{11}$, $R^{12}$, $R^{13}$ and $R^{14}$ are aryl, aralkyl, alkaryl, alkyl or cycloalkyl groups, or phenyl or alkyl groups substituted with groups such as $NH_2$, $NR_2$, $NR_3^+Y^-$ ($R=C_1$ to $C_4$ alkyl, Y=anions such as halides), OH, COOH, $SO_3H$, halogens or $CF_3$, wherein $R^{11}$, $R^{12}$ $R^{13}$ and $R^{14}$ are the same or different, wherein $R^{11}$ and $R^{12}$ as well as $R^{13}$ and $R^{14}$, respectively, may be two alkyl substituents linked to one another to form phosphacycloalkanes, M represents transition metals Ti, V, Cr, Mn, Fe, Co, Ni, Cu, Zr, Nb, Mo, Ru, Rh, Pd, Ag, Hf, Ta, W, Re, Os, Ir, Pt, Au in different oxidation stages, X represents up to three anions or ligands (n=0, 1, 2, 3), such as halides ($F^-$, $Cl^-$, $Br^-$, $I^-$), cyanide, acetate, propionate, trifluoroacetate, acetylacetonate, hexafluoroacetylacetonate, sulfate, alkylsulfonate, arylsulfonate, trifluoromethanesulfonate, hydride, alkyl, aryl, carbon monoxide, nitrosyl, trialkylphosphine, triarylphosphine, trialkylphosphite, triarylphosphite, ethylene, olefins, acetylenes, cyclopentadienyl, benzene, which are bound to the transition metal M, are altogether very active catalysts and thus can be employed for the catalysis of various reactions.

The novel phosphine ligands (I) wherein $R^1$, $R^2$, $R^3$, $R^6$, $R^7$, $R^8$ and $R^9$ represent hydrogens or, preferably $R^9$ or $R^2$ and $R^7$, represent one or two alkyl or alkoxy groups each having from 1 to 12 carbon atoms or aryl, $NH_2$, $NR_2$, $NR_3^+Y^-$ ($R=C_1$ to $C_4$ alkyl, $Y^-$=anions such as halides), OH, COOH, $SO_3H$, halogens or $CF_3$, and wherein $R^1$, $R^2$, $R^3$, $R^6$, $R^7$, $R^8$ and $R^9$=H or, preferably $R^9$ or $R^2$ and $R^7$, represent one or two alkyl, alkoxy or aryl groups substituted with groups such as $NH_2$, $NR_2$, $NR_3^+Y^-$ ($R=C_1$ to $C_4$ alkyl, $Y^-$=anions such as halides), OH, COOH, $SO_3H$, halogens or $CF_3$, wherein $R^{11}$, $R^{12}$, $R^{13}$ and $R^{14}$ are aryl, aralkyl, alkaryl, alkyl or cycloalkyl groups, or phenyl or alkyl groups substituted with groups such as $NH_2$, $NR_2$, $NR_3^+Y^-$ ($R=C_1$ to $C_4$ alkyl, $Y^-$=anions such as halides), OH, COOH, $SO_3H$, halogens or $CF_3$, wherein $R^{11}$, $R^{12}$, $R^{13}$ and $R^{14}$ are the same or different, wherein $R^{11}$ and $R^{12}$ as well as $R^{13}$ and $R^{14}$, respectively, are two alkyl substituents bonded to one another to form phosphacycloalkanes, are very tightly coordinated to the metal centers and thus inhibit undesirable reactions at the phosphorus centers which are irreversible under the conditions of catalysis. ligands (I) are distinct from the as yet known diphosphane ligands by a number of properties. The fused, tricyclic, completely aromatic core structure of the acridine to which the phosphorus substituents are directly attached provides a planar and particularly rigid structure for the ligands. The acridine nitrogen positioned between the two phosphorus atoms constitutes a third coordination site so that the diphosphine compounds (I) serve as tridentate ligands for transition metals and thus exhibit a particularly strong metal-ligand coordination. In contrast to the pyridine ligand (III, R=phenyl), the acridine ligands (I) are triarylphosphines in the case where $R^{11}$ to $R^{14}$=phenyl or aryl, being characterized by a high resistance to oxygen as compared to the very oxygen-sensitive phosphines with one or more aliphatic phosphorus substituents.

With the novel 4,5-diphosphinoacridines (I, "acriphos") and transition metal compounds, according to the invention, novel catalysts can be prepared which have clearly improved properties as compared to prior catalysts made from transition metal compounds and phosphine ligands. Thus, for example, the 1:1 complex of palladium(II) chloride and "acriphos" (I, $R^1$ to $R^9$=H, $R^{11}$ to $R^{14}$=phenyl) catalyzes carbon monoxide conversion via the water-gas shift reaction (WGSR) without the formation of phosphine oxides occurring at the ligand in the presence of water, as set forth above, and thus the catalyst system very quickly losing its activity. The strong metal-ligand bonding of the "acriphos" ligands (I) is advantageous for the stability of catalysts. For example, the nickel(II) catalysts heretofore used for hydrocyanogenation often very quickly lose their activity due to the competing formation of nickel(II) cyanide [M. Kranenburg, P. C. J. Kamer, P. W. N. M. van Leeuwen, D. Vogt and W. Keim, *J. Chem. Soc. Chem. Commun.* 1995, 2177].

In formulas (I) for the ligands and (II) for the transition metal complexes, the substituents $R^{11}$ to $R^{14}$ at the phosphorus atoms represent aryl, aralkyl, alkaryl, alkyl or cycloalkyl groups. They may be the same or different. Two alkyl substituents of one phosphorus atom may also be linked to one another to form, together with the phosphorus atom, cyclic phosphacycloalkanes as substituents of the 4,5-substituted acridine. The acridine substituents $R^1$, $R^2$, $R^3$, $R^6$, $R^7$, $R^8$ and $R^9$ are either hydrogens or at least one or two of said substituents, preferably $R^9$ or $R^2$ and $R^7$, are groups which increase the solubility of ligands (I) and transition metal complexes (II) in certain solvents or reaction media. Such groups include, e.g., alkyl and alkoxy groups with from 1 to 12 carbon atoms, groups such as $NH_2$, $NR_2$ and $NR_3^+X^-$ ($R=C_1$ to $C_4$ alkyl, $X^-$=anions such as halides), OH, COOH, $SO_3H$, halogens or $CF_3$ as well as alkyl or aryl groups which are in turn substituted with groups such as $NH_2$, $NR_2$ and $NR_3^+X^-$ ($R=C_1$ to $C_4$ alkyl, $X^-$=anions such as halides), OH, COOH, $SO_3H$, halogens or $CF_3$. Such groups may also be attached to the phosphorus substituents $R^{11}$ to $R^{14}$, e.g., $R^{11}$, $R^{12}$, $R^{13}$ and $R^{14}$ may represent one to four phenyl or alkyl residues having such groups as substituents.

The transition metal compounds used together with the diphosphine ligands (I) for the novel catalyst systems (II)

may be compounds of the following transition metals in different oxidation stages: Ti, V, Cr, Mn, Fe, Co, Ni, Cu, Zr, Nb, Mo, Ru, Rh, Pd, Ag, Hf, Ta, W, Re, Os, Ir, Pt, Au. In the complex compounds (II), up to three anions or ligands ($X_n$, n=0, 1, 2, 3) may be bound to the transition metal M, depending on the kind of metal and its oxidation stage. Such anions or ligands include, for example, halides ($F^-$, $Cl^-$, $Br^-$, $I^-$), cyanide, acetate, propionate, trifluoroacetate, acetylacetonate, hexafluoroacetylacetonate, sulfate, alkylsulfonate, arylsulfonate, trifluoromethanesulfonate, hydride, alkyl, aryl, carbon monoxide, nitrosyl, trialkylphosphine, triarylphosphine, trialkylphosphite, triarylphosphite, ethylene, olefins, acetylenes, cyclopentadienyl, benzene. Compounds (II) may be neutral, cationic or anionic complex compounds.

The catalyst systems may be either stoichiometric ligand transition metal complexes, such as the complex compounds VIII–XII set forth below, or be formed in situ from mixtures of ligands (I) and transition metal compounds. In the latter case, the ratio of ligand/metal is generally between 0.1 and 100, preferably between 0.5 and 10. It may also be advantageous to additionally use a cocatalyst to enhance the reactivity of the catalyst system. For example, the cocatalyst may be a Lewis acid (e.g., $AlCl_3$, $BF_3$, $SnCl_2$, $ZnCl_2$, $SbF_3$, $SbF_5$) or a soluble silver (I) compound of which 1 to 10 equivalents are added to the transition metal compound.

The catalysts according to the invention can be employed for carbon monoxide conversion via the water-gas shift reaction (WGSR: $CO+H_2O \rightarrow CO_2+H_2$) and for the catalysis of reactions such as hydroformylation, carbonylation, carboxylation, hydrogenation, hydrocyanogenation, hydrosilylation, polymerization, isomerization, cross-couplings and metathesis.

The present invention preferably relates to the preparation of complex compounds (II) through the reaction of 4,5-bis(diphenylphosphino)acridine (Ia) with transition metal compounds in different oxidation stages. This ligand has been used to prepare the following transition metal complexes by reactions with bis(benzonitrile)palladium(II) chloride, nickel(II) chloride hexahydrate, platinum(II) chloride, carbonylhydridotris(triphenylphosphine)rhodium(I) and 2,5-norbornadiene-molybdenum(0) tetracarbonyl in organic solvents, such as hydrocarbons, preferably benzene and toluene, ethers, preferably diethyl ether, tetrahydrofuran, dimethoxyethane, 1,4-dioxan, carbon tetrachloride, chlorohydrocarbons, preferably dichloromethane and chloroform, alcohols, preferably butanol, acetone, acetonitrile, dimethylformamide, at temperatures of between $-100°$ C. and $+200°$ C., preferably between $0°$ C. and $100°$ C., for example, at from room temperature to $30°$ C.: 4,5-bis(diphenylphosphino)acridinepalladium(II) chloride (VIII), 4,5-bis(diphenylphosphino)acridinenickel(II) chloride (IX), bis-[4,5-bis(diphenylphosphino)acridinechloroplatinum(II)] tetra-chloroplatinate(II) (X), 4,5-bis(diphenylphosphino)acridine-carbonylhydridorhodium(I) (XI) and 4,5-bis(diphenylphosphino)-acridinemolybdenum(0) tricarbonyl (XII).

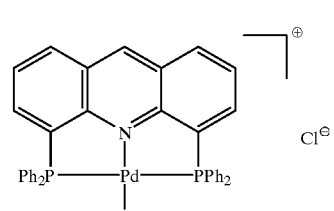

VIII

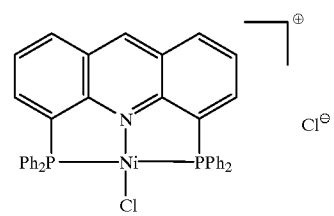

IX

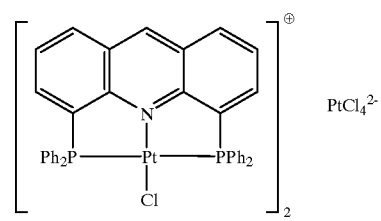

X

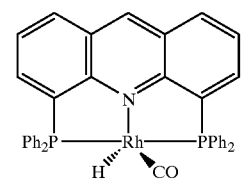

XI

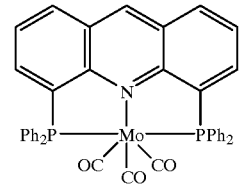

XII

From the spectroscopical data, it can be derived that the ligand 4,5-bis(diphenylphosphino)acridine is in all cases coordinated to the transition metals through both its two phosphorus atoms and its acridine nitrogen. In the case of the molybdenum tricarbonyl complex (XII), evidence of a threefold, approximately "T"-shaped planar ligand-metal coordination was additionally furnished by a single-crystal X-ray crystallographic study (FIG. 1, distances P . . . P: 4.732 Å; Mo . . . P: 2.405 Å and 2.426 Å; Mo . . . N: 2.290 Å). The ionic structure of complexes (VIII), (IX) and (X) is indicated by the mass spectra with the molecular ions of the complex cations, as well as by conductivity measurements.

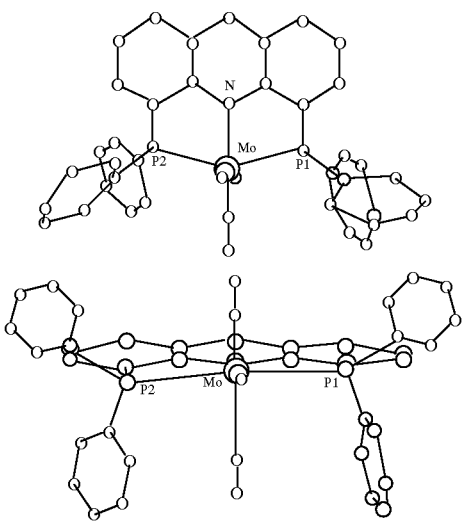

FIG. 1: Single-crystal X-ray crystallographic structure of 4,5-bis(diphenylphosphino)acridinemolybdenum(0) tricarbonyl (XII). Left: top view of the acridine moiety. Right: Front elevational view of the molybdenum tricarbonyl moiety.

According to the invention, the transition metal complexes (II) described, preferably the metal complexes (VIII) to (XII) described, can be used as catalysts. For example, 4,5-bis(diphenylphosphino)acridinepalladium(II) chloride (VIII) in solution in 9:1 n-butanol/water is capable of catalyzing the carbon monoxide conversion via the WGSR under neutral conditions (i.e., without the addition of acid or base) at a relatively low temperature of 130° C. already [for a review of the homogeneous catalysis of WGSR, see: R. M. Laine and E. J. Crawford, *J. Mol. Catal.* 44 (1988) 357]. The catalyst retains its activity even after the reaction has been interrupted (cooling, removal of gas, renewed pressurizing with carbon monoxide and reheating). The oxidation of the diphosphine ligand (I) by divalent transition metals in the presence of water as mentioned above is completely eliminated or at least much decelerated. The example of WGSR catalysis by the palladium complex (VIII) in neutral solution exhibits great progress and clear advantages if compared with WGSR catalyses described in the literature with catalyst systems made from transition metal compounds and phosphine ligands. This is evident, e.g., in a comparison with the catalyst system described by Zudin et al. consisting of palladium(II) acetate and triphenylphosphine which requires a very large excess of the phosphine ligand (metal to ligand ratio of from 1:50 to 1:100) and the highly acidic and thus very corrosive reaction medium of 4:1 trifluoroacetic acid/water [V. N. Zudin, V. A. Likholobov, Yu. I. Yermakov and N. K. Yeremenko, *Kinet. Catal.* (*Transl. of Kinet. Katl.*) 18 (1977) 440; V. N. Zudin, V. D. Chinakov, V. M. Nekipelov, V. A. Rogov, V. A. Likholobov and Yu. I. Yermakov, *J. Mol. Catal.* 52 (1989) 27–48].

The present invention also relates to the synthesis of the 4,5-diphosphinoacridines (I). These ligands (I) can be prepared by the reaction of heretofore unknown 4,5-dihaloacridines (halo=F, Cl, Br, I) with alkali metal phosphides [$R_2P^-M^+$(R=alkyl, phenyl or aryl; $M^+$=$Li^+$, $Na^+$, $K^+$, $Rb^+$, $Cs^+$)] in aprotic organic solvents, such as hydrocarbons, preferably toluene, ethers, preferably diethyl ether, tetrahydrofuran, dimethoxyethane, 1,4-dioxan, oligomeric ethylene glycol dimethyl ethers, hexamethylphosphoric triamide, N-methyl-2-pyrrolidinone, preferably in 1,4-dioxane, at temperatures of between −100° C. and +200° C., preferably between 0° C. and +150° C., or by the reaction of the 4,5-dihaloacridines (halo=F, Cl, Br, I) with chlorophosphines [$R_2PCl$ (R=alkyl, phenyl or aryl)] and magnesium in aprotic organic solvents, such as hydrocarbons, preferably toluene, ethers, preferably diethyl ether, tetrahydrofuran, dimethoxyethane, 1,4-dioxan, oligomeric ethylene glycol dimethyl ethers, hexamethylphosphoric triamide, N-methyl-2-pyrrolidinone, preferably in tetrahydrofuran, at temperatures of between −100° C. and +100° C., preferably between 0° C. and +100° C. Preferably, ligands (I) are prepared by the reaction of 4,5-difluoroacridine (XIII) with potassium phosphides [$R_2P^-K^+$(R=alkyl, phenyl or aryl)] or by the reaction of 4,5-dibromoacridine (XIX) with chlorophosphines [$R_2PCl$ (R=alkyl, phenyl or aryl)] and magnesium in such aprotic organic solvents. For example, 4,5-bis(diphenylphosphino)acridine (Ia) was obtained by the reaction of 4,5-difluoroacridine (XIII) with two equivalents of potassium diphenylphosphide ($Ph_2P^-K^+$) in 1,4-dioxane at temperatures of between 0° C. and 100° C.:

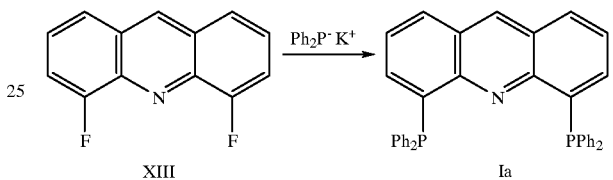

The required 4,5-difluoroacridine (XIII) which has not been known heretofore can be prepared from 2-amino-3-fluorobenzoic acid (XIV) and 2-fluoroiodobenzene (XV) in a four-step synthesis: (XIV) and (XV) can be reacted to 3-fluoro-2-(2-fluorophenylamino)benzoic acid (XVI) in a copper-catalyzed coupling reaction in the presence of potassium carbonate in solvents such as alcohols, ethylene glycols, ether, tetrahydrofuran, 1,4-dioxan, dimethoxyethane, preferably in cyclohexanol, at temperatures of between 20° C. and 200° C., preferably at from 100° C. to 160° C.:

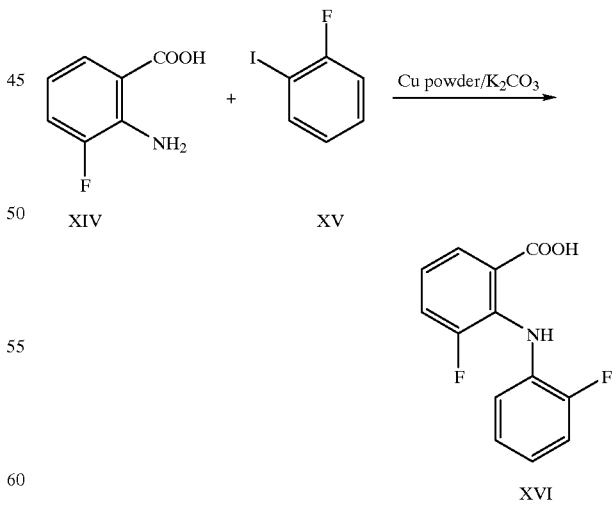

Subsequently, XVI can be cyclized in phosphoryl chloride at temperatures of between 50° C. and 150° C. to form 9-chloro-4,5-difluoroacridine (XVII). Retaining the 4- and 5-fluoro substituents, the 9-chloro substituent can be removed from (XVII) by reacting (XVII) with p-toluenesulfonic hydrazide in hydrocarbons or chlorohydrocarbons, preferably in chloroform, at temperatures of between 0° C. and 100° C. to form 9-(p-toluenesulfonyl hydrazide)-4,5-difluoroacridinium hydrochloride (XVIII), and then decomposing (XVIII) with aqueous sodium hydroxide in ethylene glycol at temperatures of between 50° C. and 200° C. to form 4,5-difluoroacridine (XIII):

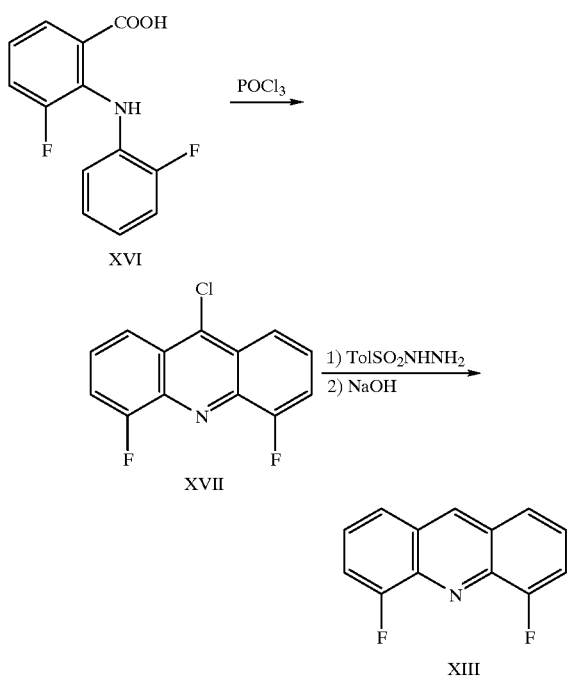

4,5-Bis(diphenylphosphino)acridine (Ia) was also obtained, for example, by the reaction of 4,5-dibromoacridine (XIX) with two equivalents of chlorodiphenylphosphine (Ph₂PCl) and two equivalents of magnesium in tetrahydrofuran at temperatures of between 20° C. and 70° C.:

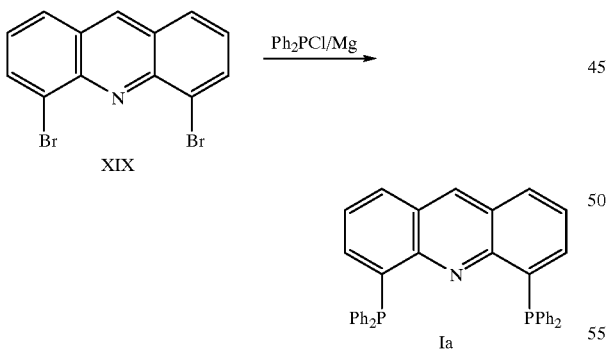

The required 4,5-dibromoacridine (XIX) which has not been known heretofore can be prepared from 3-bromo-2-iodobenzoic acid (XX) and 2-bromoaniline (XXI) in a four-step synthesis: (XX) and (XXI) can be converted with sodium hydride to the corresponding sodium compounds which can be reacted to 3-bromo-2-(2-bromophenylamino)benzoic acid (XXII) in the presence of copper powder in solvents such as ether, tetrahydrofuran, 1,4-dioxane, dimethoxyethane, preferably in tetrahydrofuran, at temperatures of between 20° C. and 150° C.:

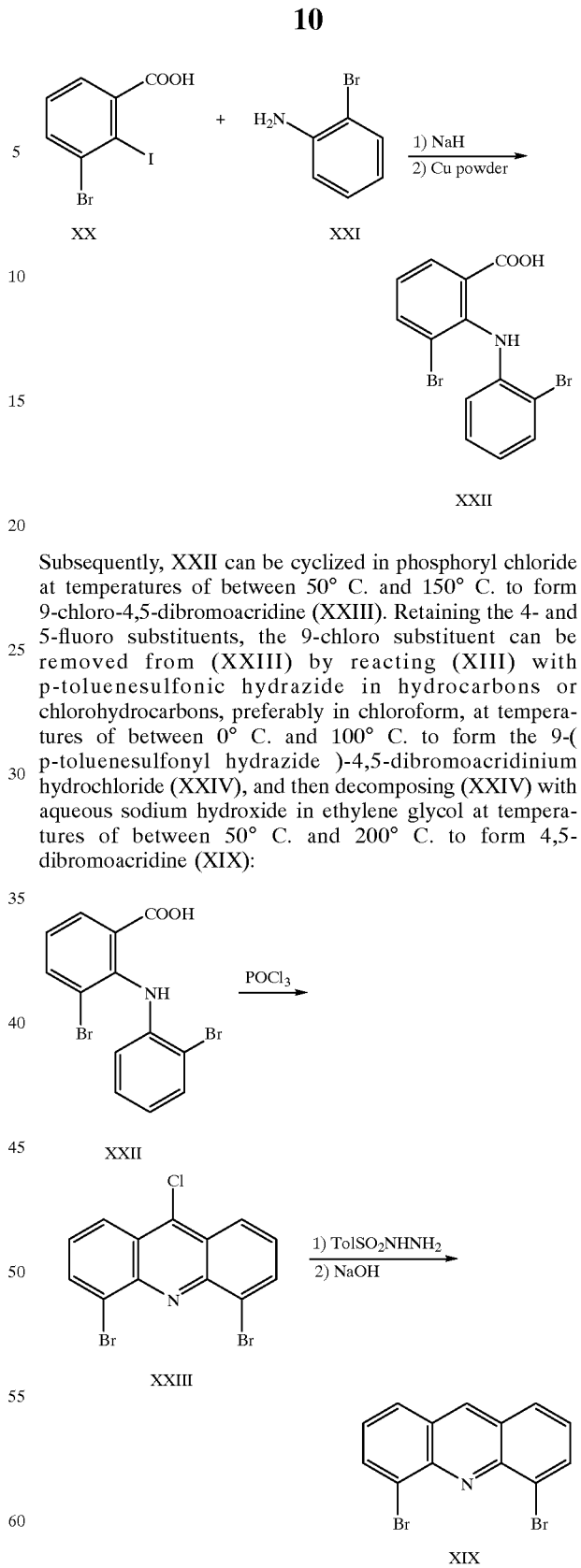

Subsequently, XXII can be cyclized in phosphoryl chloride at temperatures of between 50° C. and 150° C. to form 9-chloro-4,5-dibromoacridine (XXIII). Retaining the 4- and 5-fluoro substituents, the 9-chloro substituent can be removed from (XXIII) by reacting (XIII) with p-toluenesulfonic hydrazide in hydrocarbons or chlorohydrocarbons, preferably in chloroform, at temperatures of between 0° C. and 100° C. to form the 9-(p-toluenesulfonyl hydrazide )-4,5-dibromoacridinium hydrochloride (XXIV), and then decomposing (XXIV) with aqueous sodium hydroxide in ethylene glycol at temperatures of between 50° C. and 200° C. to form 4,5-dibromoacridine (XIX):

With the syntheses of 4,5-difluoroacridine (XIII) and 4,5-dibromoacridine (XIX) according to the invention, intermediates for further syntheses of 4,5-disubstituted acridines which have been hardly accessible to date are available.

EXAMPLES OF TRANSITION METAL COMPLEXES OF 4,5-BIS (DIPHENYLPHOSPHINO)ACRIDINE (I, R=PHENYL)

Example 1
4,5-Bis(diphenylphosphino)acridinepalladium(II) chloride (VIII):

To a solution of 0.15 g (0.27 mmol) of 4,5-bis (diphenylphosphino)acridine (Ia) in 30 ml of anhydrous dichloromethane was added dropwise a solution of 0.10 g (0.26 mmol) of bis(benzonitrile)palladium(II) chloride in 8 ml of anhydrous dichloromethane at room temperature. The resulting red solution was stirred at room temperature for 16 hours. After concentrating the mixture to a volume of 2 ml, 10 ml of tetrahydrofuran and 10 ml of n-pentane were added. The resulting precipitate was filtered off, washed twice with n-pentane and dried under high vacuum to obtain 0.16 g (81% of theory) of 4,5-bis(diphenylphosphino) acridinepalladium(II) chloride (VIII) as a light-brown solid which will decompose from 185° C. (DSC)

$C_{37}H_{27}NP_2PdCl_2$ (724.90 g mol$^{-1}$) calc. 61.31% C, 3.75% H, 1.93% N, 8.55% P, 9.78% Cl, 14.68% Pd found 61.15% C, 3.94% H, 1.85% N, 8.52% P, 9.98% Cl, 14.65% Pd

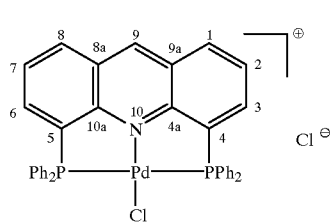

VIII

MS (ESI, CH$_2$Cl$_2$, pos. ions): m/z=688 ([M—Cl]$^\oplus$ with $^{35}$Cl and $^{106}$Pd, isotope pattern as calc.). IR (KBr): ν=3047 cm$^{-1}$ (w, ν[C—H]; 1518 (m), 1435 (s) and 1418 (m, ν[C=C]); 1096 (s); 746 (s) and 691 (s, γ[C—H]); 519 (vs). 31P NMR (81 MHz, CDCl$_3$, external standard 85% phosphoric acid): δ=32.7 (s). $^1$H NMR (400 MHz, CD$_2$Cl$_2$): δ=10.97 (s br., $^1$H, 9-H); 9.18 (d br.), 8.36 ("q" br.) and 8.00 ("t" br.) [ABCXX' spin system with X=X'=$^{31}$P, $^4$J$_{AB}$ n.d., $^3$J$_{AC}$≈8 Hz,. $^3$J$_{BC}$≈7 Hz, Σ"J$_{BX(X')}$≈10 Hz, 2H each for 1-, 8-H (A), 3-, 6-H (B), 2-, 7-H (C)]; 7.89–7.76 (m, 8H, phenyl H$_{ortho}$), 7.66–7.56 (m, 12H, phenyl H). $^{13}$C NMR (50 MHz, CDCl$_3$): δ(multiplicity with respect to $^1$J$_{CH}$, apparent "multiplicity" by coupling with $^{31}$P)=153.7 (s, "t" with Σ"J$_{CP}$=24.4 Hz, C-4a, -10a), 148.2 (d, s, C-9), 144.1 (d, s, C-1, -8 or C-3, -6), 136.8 (d, s, C-1, -8 or C-3, -6), 133.7 (d, "t" with Σ"J$_{CP}$=14.2 Hz, phenyl C$_{ortho}$), 132.7 (d, s, phenyl C$_{para}$), 130.6 (s, "t" with Σ"J$_{CP}$=40.7 Hz, C-4, -5), 129.7 (d, "t" with Σ"J$_{CP}$=10.2 Hz, phenyl C$_{meta}$), 129.4 (s, "t" with Σ"J$_{CP}$=8.1 Hz, C-8a, -9a), 128.1 (d, "m" with Σ"J$_{CP}$=8.5 Hz, C-2, -7), 126.8 (s, "t" with Σ"J$_{CP}$=52.9 Hz, phenyl C$_{ipso}$)

Example 2
4,5-Bis(diphenylphosphino)acridinenickel(II) chloride (IX):

To a suspension of 0.22 g (0.40 mmol) of 4,5-bis (diphenylphosphino)acridine (Ia) in 60 ml of n-butanol was added dropwise a solution of 0.10 g (0.42 mmol) of nickel (II) chloride hexahydrate in 10 ml of n-butanol at room temperature. The mixture was subsequently stirred at room temperature for 30 h. The resulting red solution was concentrated to a volume of 5 ml, and 15 ml of n-pentane was added. The resulting precipitate was filtered off, washed twice with n-pentane and dried under high vacuum to obtain 0.18 g (63% of theory) of 4,5-bis(diphenylphosphino) acridinenickel(II) chloride (IX) with two molecules of crystal water as a rust-red powder which will decompose from 150° C.

$C_{37}H_{27}NP_2NiCl_2 \cdot 2H_2O$ (713.20 g mol$^{-1}$) calc. 62.31% C, 4.38% H, 1.96% N, 8.69% P, 9.94% Cl, 8.23% Ni found 61.79% C, 4.31% H, 1.96% N, 8.74% P, 10.42% Cl, 8.67% Ni

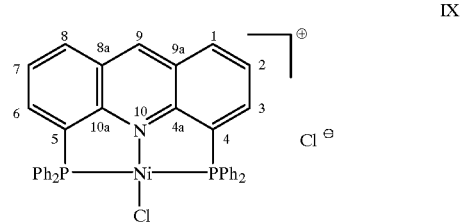

IX

MS (ESI, CH$_2$Cl$_2$, pos. ions): m/z=640 ([M—Cl]$^\oplus$ with $^{35}$Cl and $^{58}$Ni, isotope pattern as calc. IR (KBr): ν=3400 cm$^{-1}$ (w, br., ν[O—H]); 3051 (w, ν[C—H]); 1517 (m), 1436 (s) and 1418 (m, ν[C=C]); 1098 (m); 745 (s) and 692 (s, γ[C—H]); 521 (vs) $^{31}$P NMR (81 MHz, CDCl$_3$, external standard 85% phosphoric acid): δ=25.6 (s). $^1$H NMR (400 MHz, CD$_2$Cl$_2$): δ=11.9 (s br., 1H, 9-H); 9.8 (s br., 2H, 1-, 8-H), 8.3 (s br., 2H, 3-, 6-H), 8.1 (s br., 2H, 2-, 7-H), 7.9 (d br., 8H, phenyl H$_{ortho}$), 7.6–7.5 (m, 12H, phenyl H).

Example 3
Bis[4,5-bis(diphenylphosphino)acridinechloroplatinum(II)] tetrachloroplatinate(II) (X):

To a solution of 150 mg (0.27 mmol) of 4,5-bis (diphenylphosphino)acridine (Ia) in 30 ml of anhydrous dichloromethane was added dropwise a suspension of 73 mg (0.27 mmol) of platinum(II) chloride in 8 ml of anhydrous dichloromethane at room temperature. The resulting red solution was stirred at room temperature for 4 d. After concentrating the mixture to a volume of 2 ml, 10 ml of tetrahydrofuran and 10 ml of n-pentane were added. The resulting precipitate was filtered off, washed twice with n-pentane and dried under high vacuum to obtain 110 mg (65% of theory) of bis[4,5-bis(diphenylphosphino) acridinechloroplatinum(II)] tetrachloroplatinate(II) (X) as a light-brown solid which will decompose from 200° C.

$C_{74}H_{54}N_2P_4Pt_3Cl_6$ (1893.11 g mol$^{-1}$): calc. 46.95% C, 2.88% H, 1.48% N, 6.54% P, 11.74% Cl, 30.91% Pt found 45.50% C, 3.00% H, 1.51% N. 6.24% P, 11.45% Cl, 30.46% Pt

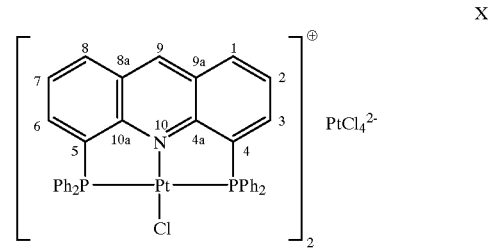

X

MS (ESI, CH$_2$Cl$_2$, pos. ions): m/z=777 ([C$_{37}$H$_{27}$NP$_2$PtCl]$^\oplus$ with $^{35}$Cl and $^{195}$Pt, isotope pattern as calc.). IR (KBr): ν=3050 cm$^{-1}$ (m, ν[C—H]; 1604 (m), 1520 (m) and 1436 (s), ν[C=C]); 1099 (m); 747 (m) and 691 (s, γ[C—H] ); 523 (vs). 31P NMR (81 MHz, CDCl$_3$, external standard 85% phosphoric acid): δ=27.2 ("t", $^1J_{195_{PtP}}$=2620 Hz). $^1$H NMR (400 MHz, CD$_2$Cl$_2$): δ=10.90 (s br., 1H, 9-H); 9.04 (d br.), 8.54 ("q" br.) and 8.01 ("t" br.) [ABCXX' spin system with X=X'$^{31}$P, $^4J_{AB}$ n.d., $^3J_{AC}$=7.8 Hz, $^3J_{BC}$≈7 Hz, Σ"$J_{BX(X')}$≈10 Hz, 2H each for 1-, 8-H (A), 3-, 6-H (B), 2-, 7-H (C)]; 7.95–7.82 (m, 8H, phenyl H$_{ortho}$), 7.67–7.48 (m, 12H, phenyl H). $^{13}$C NMR (50 MHz, CD$_2$Cl$_2$): δ(multiplicity with respect to $^1J_{CH}$, apparent "multiplicity" by coupling with $^{31}$P)=154.4 (s, "t" with Σ"$J_{CP}$=22.0 Hz, C-4a, -10a), 146.8 (d, s br., C-9), 144.8 (d, s br., C-1, -8 or C-3, -6), 136.4 (d, s br., C-1, -8 or C-3, -6), 134.1 (d, "t" with Σ"$J_{CP}$=14.0 Hz, phenyl C$_{ortho}$), 133.0 (d, s, phenyl C$_{para}$), 131.5 (s, "t" with Σ"$J_{CP}$=51.0 Hz, C-4, -5), 129.7 (d, "t" with Σ"$J_{CP}$=10.2 Hz, phenyl C$_{meta}$), 128.9 (d, "m" with Σ"$J_{CP}$=8.0 Hz, C-2, -7), 128.9 (s, C-8a, -9a), 127.3 (s, "t" with Σ"$J_{CP}$=61.5 Hz, phenyl C$_{ipso}$)

Example 4
4,5-Bis(diphenylphosphino)acridinecarbonylhydridorhodium(I) (XI):

To a suspension of 200 mg (365 pmol) of 4,5-bis(diphenylphosphino)acridine (Ia) in 30 ml of anhydrous toluene was added a solution of 335 mg (365 pmol) of carbonylhydrido-tris(triphenylphosphin)rhodium(I) in 25 ml of anhydrous toluene. The resulting mixture was stirred at 30° C. for 4 h. The solvent was then distilled off in vacuo, and the residue was suspended in 5 ml of tetrahydrofuran. After the addition of 10 ml of n-pentane, the precipitate was filtered off, washed with n-pentane and dried under high vacuum to obtain 120 mg of an orange-yellow solid which consists of 4,5-bis(diphenylphosphino)acridinecarbonylhydridorhodium(I) (XI) as determined by mass-spectrometrical and IR-spectroscopical analysis.

$C_{38}H_{28}NP_2ORh$ (679.50 g mol$^{-1}$): calc. 679.069417 u found 679.064144 u (high resolution MS)

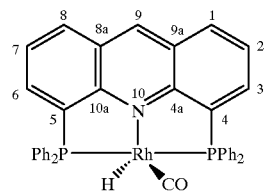

XI

MS (EI, 70 eV, VT 330° C.): m/z (%)=679 (100, M$^{⊕}$*)=, 651 (72, [M—CO]$^{⊕}$*), 570 (24), 494 (53, [M—PPh$_2$]$^{⊕}$), 388 (28), 254 (18), 78 (20) IR (KBr): ν=3053 cm$^{-1}$ (w, ν[C—H]); 1953 (vs, ν[C≡O]); 1573 (m), 1434 (s) and 1413 (vs, ν[C=C]); 1097 (m); 742 (s) and 693 (s, γ[C—H]); 515 (s).

Example 5
4,5-Bis(diphenylphosphino)acridinemolybdenum(0) tricarbonyl (XII):

To a suspension of 150 mg (0.274 mmol) of 4,5-bis(diphenylphosphino)acridine (Ia) in 25 ml of toluene was added dropwise a solution of 82 mg (0.273 mmol) of 2,5-norbornadienemolybdenum(0) tetracarbonyl in 10 ml of toluene at room temperature. The mixture was stirred at room temperature for 17 h. The solvent was then distilled off, and the residue dissolved in 10 ml of methylene chloride. To the dark-green solution was added 20 ml of n-pentane. The resulting precipitate was filtered off and dried under high vacuum to obtain 30 mg (15% of theory) of 4,5-bis(diphenylphosphino)acridinemolybdenum(0) tricarbonyl (XII) as a dark-green powder which will decompose from 345° C. (DSC).

$C_{40}H_{27}NP_2MoO_3$ (727.55 g mol$^{-1}$) calc. 66.04% C, 3.74% H, 1.93% N, 8.51% P, 13.19% Mo found 65.87% C, 3.71% H, 2.03% N, 8.58% P, 13.31% Mo

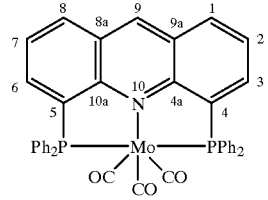

XII

MS (EI, 70 eV, VT 240° C.): m/z (%)=729 (<1, M$^{⊕}$ with $^{98}$Mo, isotope pattern as calc.), 701 (9, [M—CO]$^{⊕}$* with $^{98}$Mo), 645 (10, [M-3CO]$^{⊕}$* .with $^{98}$Mo), 547 (8, [M—Mo-3CO]$^{⊕}$*), 154 (10), 78 (88), 77 (21), 51 (17), 39 (13), 28 (100). IR (KBr): ν=3054 cm$^{-1}$ (w, ν[C—H]); 1957 (s), 1850 (vs), 1810 (vs) and 1801 (vs, ν[C≡O]); 1603 (m), 1507 (m) and 1433 (m, ν0[C=C]); 1088 (m); 743 (m) and 694 (s, γ[C—H]); 513 (s). 31P NMR (81 MHz, CD$_2$Cl$_2$, external standard 85% phosphoric acid): 58.6 (s) $^1$H NMR (200 MHz, CD$_2$Cl$_2$): δ=9.00 (s br., 1H, 9-H); 8.19 (d br., 2H), 8.07 (m, 2H) [AB portion of an ABCXX' spin system with X=X'=$^{31}$P $^4J_{AB}$≈1 Hz, $^3J_{AC}$=8.0 Hz, $^3J_{BC}$≈7 Hz, Σ"$J_{BX(X')}$≈7 Hz, 2H each for 1-, 8-H (A), 3-, 6-H (B); 7.72–7.57 [m, 10H, 2-, 7-H (C portion of the ABCXX' spin system) and phenyl H$_{ortho}$], 7.44–7.35 (m, 12H, phenyl H). $^{13}$C NMR (50 MHz, CD$_2$Cl$_2$): δ(multiplicity with respect to $^1J_{CH}$, apparent "multiplicity" by coupling with $^{31}$P)=215.9 (s, t with $^2J_{CP}$=30 Hz, C=O), 155.0 (s, "t" with Σ"$J_{CP}$=27 Hz, C-4a, -10a), 141.5 (d, s, C-3, -6), 140.0 (s, "t" with Σ"$J_{CP}$=24 Hz, C-4, -5), 139.6 (s, "t" with Σ"$J_{CP}$=35 Hz, phenyl C$_{ipso}$), 139.2 (d, t with $^6J_{CP}$=3 Hz, C-9), 132.8 (d, "t" with Σ"$J_{CP}$=13 Hz, phenyl C$_{ortho}$), 132.1 (d, s, C-1, -8), 129.4 (d, s, phenyl C$_{para}$), 128.6 (d, "t" with Σ"$J_{CP}$=10 Hz, phenyl C$_{meta}$), 128.3 (s, "t" with Σ"$J_{CP}$=8 Hz, C-8a, -9a), 126.4 (d, "t" with Σ"$J_{CP}$=5 Hz, C-2, -7).

With crystals obtained from a solution in dichloromethane/n-pentane, the single-crystal X-ray crystallographic structure of compound (XII) could be determined (FIG. 1).

Example 6
Catalysis of the water-gas shift reaction: CO+H$_2$O→CO$_2$+H$_2$):

A steel autoclave (V4A steel, volume 100 ml, equipped with a manometer, valve, magnetic stirring and heater) was filled under an argon atmosphere with 50.0 mg (0.07 mmol) of 4,5-bis-(diphenylphosphino)acridinepalladium(II) chloride (VII), 18 ml of n-butanol and 2 ml of distilled water, and sealed. The autoclave was first flushed by pressurizing with carbon monoxide and subsequently releasing the pressure. After pressurizing with 30 bar of carbon monoxide (pressure at room temperature), the autoclave was heated at 130° C. for 15.5 h with stirring. After cooling down to room temperature, a pressure of 34 bar was read. Through a valve, a gas sample was removed and analyzed by mass spectrometry: 74.8 mole % CO, 18.1 mole % H$_2$, 7.1 mole % CO$_2$. According to the formula $$\text{degree of conversion} = \frac{\text{mole \% H}_2}{\text{mole \% H}_2 + \text{mole \% CO}},$$

a degree of conversion of 19.5% was calculated. The absolute amount of hydrogen formed is calculated from the volume of the autoclave and the partial pressures of the gases according to the general gas equation to be 20 mmol. Related to the amount of catalyst employed, a number of the catalysis cycles performed (turnover number) of 285 was obtained.

The autoclave which still contained the catalyst in n-butanol/water was then flushed with carbon monoxide, pressurized with 30 bar of carbon monoxide for the second time, and heated at 130° C. for 16 h with stirring. After cooling down to room temperature, the pressure was 33 bar. From the gas analysis (87.1 mole % CO, 7.1 mole % $H_2$, 5.8 mole % $CO_2$), a degree of conversion of 7.5% and a turnover number of 110 were calculated as set forth above.

Example 7
Synthesis of 4,5-bis(diphenylphosphino)acridine (Ia):

To a solution of 0.51 g (2.37 mmol) of 4,5-difluoroacridine (XIII) in 50 ml of 1,4-dioxane was added dropwise 9.3 ml (4.65 mmol) of a 0.5 M solution of potassium diphenylphosphide ($Ph_2P^-K^+$) in tetrahydrofuran at room temperature. After the addition was completed, the mixture was heated at reflux for one hour. After cooling, 30 ml of distilled water was added to the brown reaction solution. The resulting precipitate was filtered off, washed thoroughly with distilled water, ethanol and n-pentane, and dried under high vacuum to obtain 1.02 g (79% of theory) of 4,5-bis(diphenylphosphino)acridine (Ia) as a yellow powder which will decompose from 255° C.

$C_{37}H_{27}NP_2$ (547.58 g $mol^{-1}$): calc. 81.16% C, 4.97% H, 2.56% N, 11.31% P found 80.67% C, 5.26% H, 2.44% N, 10.53% P

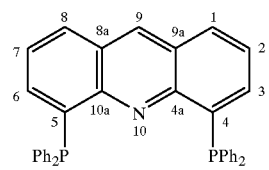

I

MS (EI, 70 eV, VT 190° C.): m/z (%)=547 (100, $M^{\oplus *}$), 360 (13) 284 (12), 283 (15). IR (KBr): ν=3060 $cm^{-1}$ (m, ν[C—H]); 1610 (m), 1510 (m) and 1435 (s, ν[C=C]); 745 (s) and 695 (s, γ[C—H])]. $^{31}$P NMR (81 MHz, $CDCl_3$, external standard 85% phosphoric acid): δ=−14.7 (s). $^1$H NMR (400 MHz, $CD_2Cl_2$): δ=8.82 (s, 1H, 9-H); 8.00 (dd), 7.40 (dd) and 7.15 (ddd) [ABCXX' spin system with X–X'= $^{31}$P, $^3J_{AB}$=8.5 Hz, $^4J_{AC}$=1.5 Hz, $^3J_{BC}$=6.8 Hz, $\Sigma^n J_{CX(X')}$=3.6 Hz, 2H each for 1-, 8-H (A), 2-, 7-H (B), 3-, 6-H (C)]; 7.30–7.20 (m, 20H, phenyl H). $^{13}$C NMR (75 MHz, $CD_2Cl_2$): δ(multiplicity with respect to $^1J_{CH}$, apparent "multiplicity" by coupling with 31P)=149.5 (s, "t", C-4a, -10a), 138.7 (s, "t", C-4, -5 or phenyl $C_{ipso}$), 138.6 (s, "t", C-4, -5 or phenyl $C_{ipso}$), 137.0 (d, s, C-9), 135.8 (d, s, C-3, -6), 134.6 (d, "d" with $\Sigma^n J_{CP}$=22.4 Hz, phenyl $C_{ortho}$), 129.2 (d, s, C-1, -8), 128.6 (d, "d" with $\Sigma^n J_{CP}$=12.2 Hz, phenyl $C_{meta}$), 128.5 (s, "d" with $\Sigma^n J_{CP}$=3.0 Hz, phenyl $C_{para}$), 126.9 (s, s, C-8a, -9a), 126.3 (d, s, C-2, -7).

With crystals obtained from a solution in dichloromethane, the single-crystal X-ray crystallographic structure of compound (I, $R^1=R^2=R^3=R^4$=phenyl) could be determined.

Example 8
Synthesis of 4,5-bis(diphenylphosphino)acridine (Ia):
A solution of 337 mg (1 mmol) of 4,5-dibromoacridine (XIX) and 440 mg (2 mmol) of chlorodiphenylphosphane ($Ph_2PCl$) in 40 ml of tetrahydrofuran was added dropwise to a boiling suspension of 72 mg (3 mmol) of magnesium powder in 20 ml of tetrahydrofuran. The mixture was then stirred at room temperature for 20 h. Hydrolysis with water and diluted hydrochlorid acid, extraction with diethyl ether, drying the ether phase over sodium sulfate and distilling off the solvent gave a brown raw product, from which 72 mg (15% of theory) of 4,5-bis(diphenylphosphino)acridine (Ia) was obtained as a yellow powder by several recrystallizations from dichloromethane and dichloromethane/hexane.

Example 9
Synthesis of 4,5-difluoroacridine (XIII):
a) 3-Fluoro-2-(2-fluorophenylamino)benzoic acid (XVI):
2-Amino-3-fluorobenzoic acid (XIV) was prepared as described in B. McKittrick, A. Failli, R. J. Steffan, R. M. Soll, P. Hughes, J. Schmid, C. C. Shaw, A. A. Asselin, R. Noureldin, and G. Gavin, *J. Heterocyclic Chem.* 27 (1990) 2151; F. Clemence, O. Le Martret and F. Delevallee, U.S. Pat. No. 4,596,875 (Jun. 24, 1986).

A mixture of 14.0 g (90.2 mmol) of 2-amino-3-fluorobenzoic acid (XIV), 12.5 g (90.4 mmol) of potassium carbonate, 21.0 g (94.6 mmol) of 2-fluoroiodobenzene (XV) and a spatula-tipfull of copper powder in 85 ml of cyclohexanol was heated at reflux for 12 hours. The solvent was then removed by steam distillation, and the aqueous residue obtained was subjected to centrifugation. The soluble centrifugate was acidified with diluted hydrochloric acid, and the resulting precipitate was filtered off and dried. Fractional sublimation of the solid under high vacuum yielded 16.0 g (71% of theory) of 3-fluoro-2-(2-fluorophenylamino) benzoic acid (XVI) as a yellow powder with a melting point of 176° C.

$C_{13}H_9F_2NO_2$ (249.22 g $mol^{-1}$): calc. 62.65% C, 3.64% H, 15.25% F, 5.62% N found 62.38% C, 3.72% H, 15.15% F, 5.66% N

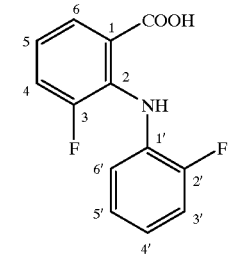

XVI

MS (EI, 70 eV, VT 90° C.): m/z (%)=249 (50, $M^{\oplus *}$, 232 (15) 231 (100, $[M—H_2O]^{\oplus *}$), 203 (15), 202 (12), 183 (15), 182 (13). IR (KBr): ν=3360 $cm^{-1}$ (m, ν[N—H]), 3060 (m, br., ν[COO—H]), 1660 (s, ν[C=O]), 1525 (s), 1260 (s, ν[C—F]), 740 (s, γ[C—H]) $^{19}$F NMR (188 MHz, [$D_6$] acetone, external standard $CFCl_3$): δ=−118.0 (s), −131.0 (s). $^1$H NMR (400 MHz, [$D_6$]acetone): δ=9.38 (s, br., 1H, N—H), 7.90 (dd, $^3J_{5-H\ 6-H}$=8.1 Hz, $^4J_{4-H\ 6-H}$≈2 Hz, 6-H), 7.39 (ddd, $^3J_{3-F\ 4-H}$=12.2 Hz, $^3J_{4-H\ 5-H}$=8.0 Hz, $^4J_{4-H\ 6-H}$≈2 Hz, 1H, 4-H), 7.16–7.02 (m, 3H), 6.99–6.88 (m, 2H). $^{13}$C NMR (100 MHz, [$D_6$] acetone): δ(multiplicity with respect to $^1J_{CH}$, coupling with $^{19}$F)=169.6 (s, d with $^4J_{CF}$=4.0 Hz, COOH), 154.9, (s, d with $^1J_{CF}$=246.6 Hz, C-3), 153.3 (s, d with $^1J_{CF}$=241.7 Hz), 134.8 (s, m, $^2J_{CF}$=11.2 Hz, C-2), 131.7 (s, m, $^2J_{CF}$=11.2 Hz, C-1'), 128,2 (d, d with $^4J_{CF}$=3.2 Hz, C-6), 124.8 (d, d with $^4J_{CF}$=3.2 Hz, C-5'), 123.0 (d, d with $^3J_{CF}$=7.2 Hz, C-5), 121.5 (d, d with $^2J_{CF}$=20.1 Hz, C-4), 121.5 (d, d with $^3J_{CF}$=5.6 Hz, C-4'), 120.4 (s, d with $^3J_{CF}$=4.0 Hz, C-1), 120.2 (d, d with $^3J_{CF}$=6.4 Hz, C-6'), 115.7 (d, d with $^2J_{CF}$=19.3 Hz, C-3'); increment calculations were performed to assist the assignment.

b) 9-Chloro-4,5-difluoroacridine (XVII):

A suspension of 31.1 g (125 mmol) of 3-fluoro-2-(2-fluorophenylamino)benzoic acid (XVI) in 110 ml (1.19 mol) of phosphoryl chloride was heated at reflux for 3.5 hours. Subsequently, the excess phosphoryl chloride was distilled off from the resulting solution at room temperature under vacuum. The remaining brown oil was dissolved in chloroform, and the solution was added dropwise to ice-cooled diluted aqueous ammonia with stirring. After the mixture had reached room temperature, the phases were separated. The aqueous phase was extracted twice with chloroform, and the combined organic phases were dried over sodium sulfate. The solvent was distilled off on a rotary evaporator, and the residue was dried under high vacuum to obtain 29.8 g of a brown-yellow solid. Fractional sublimation under high vacuum yielded 25.4 g (81% of theory) of 9-chloro-4,5-difluoroacridine (XVII) in analytically pure form as a yellow powder with a melting point of 183–186° C.

$C_{13}H_6F_2ClN$ (249.65 g mol$^{-1}$) calc. 62.55% C, 2.42% H, 15.22% F, 5.61% N, 14.20% Cl found 62.38% C, 2.51% H, 15.19% F, 5.69% N, 14.16% Cl

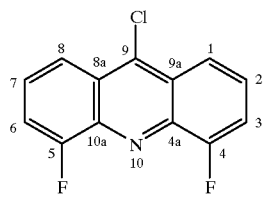

XVII

MS (EI, 70 eV, VT 60° C.): m/z (%)=249 (100, M$^\oplus$, $^{35}$Cl, isotope pattern as calc.), 213 (10). IR (KBr): ν=3050 cm$^{-1}$(m, ν[C— H], 1630 s, 1550 (s, ν[C=C]), 1330 (s), 1250 (s, ν[C—F]), 740 (s, γ[C—H]). $^{19}$F NMR (188 MHz, CDCl$_3$, external standard CFCl$_3$): δ=−122.4 (s). $^1$H NMR (400 MHz, CDCl$_3$): δ=8.18 (d"t"), 7.58 (ddd), 7.51 (ddd) [ABCX spin system with X=$^{19}$F, $^3J_{CX}$=10.1 Hz, $^3J_{AB}$=8.7 Hz, $^3J_{BC}$=7.4 Hz, $^3J_{AC}$=1.3 Hz, $^4J_{AX}$=1.3 Hz, $^3J_{BX}$=5.0 Hz, 2H each for 1-, 8-H (A), 2-, 7-H (B), 3-, 6-H (C)].

c) 4,5-Difluoroacridine (XIII)

i) Synthesis of 9-(p-toluenesulfonyl hydrazide)-4,5-difluoroacridinium hydrochloride (XVIII):

A solution of 25.4 g (102 mmol) of 9-chloro-4,5-difluoroacridine (XVII) in 300 ml of anhydrous chloroform was added dropwise to a suspension of 20.7 g (111 mmol) of para-toluenesulfonic hydrazide in 200 ml of anhydrous chloroform stirred at 50° C. After cooling to room temperature, the suspension was stirred for 2 d. The precipitate was filtered off, washed with a little chloroform and dried under high vacuum to obtain 38.7 g (87% of theory) of 9-(p-toluenesulfonyl hydrazide)-4,5-difluoroacridinium hydrochloride (XVIII) as a bright yellow solid.

MS (EI, 70 eV, VT 80° C.): m/z (%)=399 (3, [M-HCl]$^\oplus$, 244 (100), 224 (13), 215 (23). IR (KBr): ν=3410 cm$^{-1}$ (w, ν[N—H]), 3230 (m, ν[N—H]), 3200–2000 (vs, br., ν[N—H]), 1345 (s, ν[S—O]), 1165 (s, ν[S—O]).

ii) Conversion to 4,5-difluoroacridine (XIII):

To a suspension of 37.7 g (86.3 mmol) of 9-(p-toluenesulfonyl hydrazide)-4,5-difluoroacridinium chloride (XVIII) in 1300 ml of ethylen glycol was added 670 ml of 3.4 M aqueous sodium hydroxide, and the mixture was heated to reflux for 2 h with stirring. After cooling, the suspension was poured into 4 l of water, and the resulting precipitate was filtered off, washed thoroughly with water, and dried under high vacuum. Sublimation under high vacuum yielded 11.6 g (62% of theory) of 4,5-difluoroacridine (X) as a yellow solid with a melting point of 193–195° C.

$C_{13}H_7F_2N$ (215.20 g mol$^{-1}$) calc. 72.56% C, 3.28% H, 17.66% F, 6.51% N found 72.30% C, 3.51% H, 17.57% F, 6.45% N

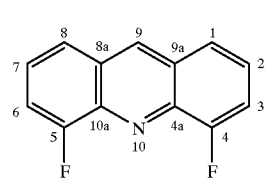

XIII

MS (EI, 70 eV, VT 80° C.): m/z (%)=215 (100, M$^\oplus$), 214 (10). IR (KBr): ν3070 cm$^{-1}$ (w, ν[C—H]), 1250 (s, ν[C—F]), 750 (s, γ[C—H]). $^{19}$F NMR (188 MHz, CDCl$_3$, external standard CFCl$_3$): δ=−123.7 (s). $^1$H NMR (400 MHz, CDCl$_3$) δ=8.79 (t, $^5J_{HF}$=1.5 Hz, 1H, 9-H), 7.80–7.74 (m, 2H, 1-, 8-H), 7.51–7.43 (m, 4H, 2-, 3-H and 6-, 7-H). $^{13}$C NMR (50 MHz, CDCl$_3$): δ(multiplicity with respect to $^1J_{CH}$, coupling with $^{19}$F)=157.8 (s, d with $^1J_{CF}$=259.8 Hz, C-4, -5), 139.7 (s, d with 2$J_{CF}$=14.0 Hz, C-4a, -10a), 135.7 (d, t with $^4J_{CF}$=6.1 Hz, C-9), 128.0 (s, s br., C-8a, -9a), 125.6 (d, d with $^3J_{CF}$=7.0 Hz, C-2, -7), 123.8 (d, "t" with $\Sigma^n J_{CF}$=6.1 Hz, C-1, -8), 113.3 (d, d with $^2J_{CF}$=19.2 Hz, C-3, -6); increment calculations were performed to assist the assignment.

Example 10

Synthesis of 4,5-dibromoacridine (XIX):

a) 3-Bromo-2-(2-bromophenylamino)benzoic acid (XXII)

3-Bromo-2-iodobenzoic acid (XX) was prepared as described in D. Twiss and R. V. Heinzelmann, *J. Org. Chem.* 15 (1950) 496.

A mixture of 16.0 g (46 mmol) of sodium 3-bromo-2-iodobenzoate [prepared from 15.0 g (46 mmol) of 3-bromo-2-iodobenzoic acid (XX) and 1.1 g (46 mmol) of sodium hydride], 19.5 g (100 mmol) of sodium 2-bromoanilide [prepared from 17.3 g (100 mmol) of 2-bromoaniline (XXI) and 2.4 g (100 mmol) of sodium hydride] and a spatulatipfull of copper powder in 100 ml of tetrahydrofuran was heated to reflux for 9 h. The solvent was distilled off, the residue extracted with 0.5 M aqueous sodium hydroxide, and the resulting suspension subjected to centrifugation. The centrifugate was acidified with diluted hydrochloric acid, the precipitated solid was filtered off and dried under high vacuum. Fractional sublimation under high vacuum yielded 6.3 g (37% of theory) of 3-bromo-2-(2-bromophenylamino) benzoic acid (XXII) as a yellow powder with a melting point of 181–182° C.

$C_{13}H_9Br_2NO_2$ (371.03 g mol$^{-1}$): calc. 42.08% C, 2.44% H, 43.07% Br, 3.78% N found 42.28% C, 2.41% H, 42.82% Br, 3.75% N

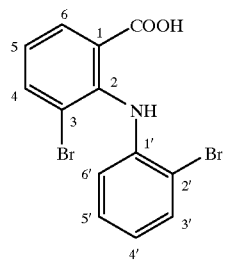

XXII

MS (EI, 70 eV, VT 120° C.): m/z (%)=369 (21, M⊕ with $^{79}Br_2$, isotope pattern as calc.), 290 (9, [M—Br]⊕ with $^{79}Br$), 272 (100, [M—Br—H$_2$O]⊕ with $^{79}Br$), 244 (12), 193 (11), 165 (29). $^1$H NMP (200 MHz, [D$_6$] acetone): δ=8.70 (s, br., 1H, NH), 8.10 (dd), 7.87 (dd), 7.19 ("t") [AMX spin system with $^3J_{MX}$=7.9 Hz, $^3J_{AX}$=7.3 Hz, $^1J_{AM}$=1.5 Hz, 1H each for 6-H (A), 4-H (M), 5-H (X)], 7.57 (dd), 7.16 (ddd), 6.83 (d"t"), 6.54 (dd) [ABCD spin system with $^3J_{AC}$=7.9 Hz, $^3J_{BD}$=7.6 Hz, $^3J_{BC}$=7.2 Hz, $^4J_{AB}$=1.5 Hz, $^4J_{CD}$=1.5 Hz, 1H each for 3'-H (A), 5'-H (B), 4'-H (C), 6'-H (D)]. $^{13}$C NMR (50 MHz, [D6]acetone): δ=168.5 (s, COOH), 143.5 (s, C-2), 142.0 (s, C-1'), 139.5 (d, C-4) 133.4 (d, C-3'), 132.0 (d, C-6), 128.4 (d, C-5'), 125.1 (C-5), 125.1 (s, C-1 or C-3), 120.1 (s, C-1 or C-3), 122.9 (d, C-4' or C-6'), 118.6 (d, C-4' or C-6'), 114.0 (s, C-2'); increment calculations were performed to assist the assignment.

b) 4,5-Dibromo-9-chloroacridine (XXIII)

A suspension of 7.43 g (20.0 mmol) of 3-bromo-2-(2-bromophenylamino)benzoic acid (XXII) in 19.5 ml (213 mmol) of distilled phosphoryl chloride was heated to reflux for 2.5 h. Subsequently, the excess phosphoryl chloride was distilled off at room temperature under vacuum. The resulting brown oil was dissolved in chloroform, and the solution was added dropwise to ice-cooled diluted aqueous ammonia with stirring. After the mixture had reached room temperature, the phases were separated. The aqueous phase was extracted twice with chloroform, and the combined organic phases were dried over sodium sulfate. The solvent was distilled off under vacuum, and the residue was dried under high vacuum. Fractional sublimation of 7.00 g of raw product under high vacuum yielded 5.5 g (74% of theory) of 4,5-dibromo-9-chloroacridine (XXIII) as an analytically pure yellow solid with a melting point of 195–196° C.

$C_{13}H_6Br_2ClN$ (371. 46 g mol$^{-1}$): calc. 42.04% C, 1.630 H, 43.02% Br, 9.54% Cl, 3.77% N found 41.97% C, 1.68% H, 43.10% Br, 9.54% Cl, 3.78% N

XXIII

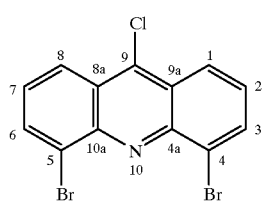

MS (EI, 70 eV, VT 100° C.): m/z (%)=369 (100, M⊕ with $^{79}Br_2$, $^{35}Cl$, isotope pattern as calc.), 290 (11, [M—Br]⊕ with $^{79}Br$, 35Cl), 211 (25, [M—2Br]⊕, $^{35}Cl$), 176 (15, [M—2Br—Cl]⊕). IR (KBr) ν=1615 cm$^-$(m), 1550 (m, ν[C═C]); 750 (s), 740 (s, γ[C—H]). $^1$H NMR (200 MHz, CDCl$_3$): δ=8.42 (dd), 8.23 (dd), 7.51 (dd) [AMX spin system with $^3J_{AX}$=8.8 Hz, $^3J_{MX}$=7.2 Hz, 4J$_{AM}$=1.3 Hz, 2H each for 1-, 8-H (A), 3-, 6-H (M), 2-, 7-H (X).

4,5-Dibromoacridine (XIX):

i) Synthesis of 9- (p-toluenesulfonyl hydrazide)-4,5-dibromoacridinium chloride (XXIV):

A solution of 5.2 g (14.0 mmol) of 4,5-dibromo-9-chloroacridine (XXIII) in 20 ml of anhydrous chloroform was added dropwise to a suspension of 2.9 g (15.6 mmol) of para-toluenesulfonic-hydrazide in 30 ml of anhydrous chloroform stirred at 50° C. The resulting suspension was stirred at room temperature for 24 h. The resulting precipitate was filtered off, washed with water and dried under high vacuum to obtain 7.1 g (91% of theory) of 9-(p-toluenesulfonyl hydrazide)-4,5-dibromoacridinium chloride as a yellow solid.

IR (KBr) ν=3370 cm$^{-1}$ (w), 3290 (m, ν[N—H)]; 2920 (m, ν[C—H]); 2750 (m br, ν[N—H]⊕); 1350 (m), 1170 (s, ν[S—O]; 745 (m, γ[C—H]).

ii) Conversion to 4,5-dibromoacridine (XIX):

To a suspension of 7.1 g (12.7 mmol) of 9-(p-toluenesulfonyl hydrazide)-4,5-dibromoacridinium chloride in 200 ml of ethylene glycol was added a solution of 13.5 g of sodium hydroxide in 100 ml of water, and the mixture was heated to reflux for 3 h with stirring. After cooling, the solution was poured into 600 ml of water. The precipitate was filtered off, washed with water and dried under high vacuum to obtain 3.9 g (91% of theory) of 4,5-dibromoacridine (XIX) as a yellow solid which was obtained in an analytically pure form upon recrystallization from toluene/cyclohexane (mp. 205° C.).

$C_{13}H_7Br_2N$ (337.01 g mol$^{-1}$): calc. 46.33% C, 2.09% H, 47.42% Br, 4.16% N found 46.18% C, 2.19% H, 47.51% Br, 4.23% N

XIX

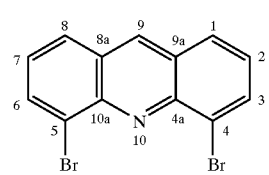

MS (EI, 70 eV, VT 120° C.): m/z (%)=335 (52, M⊕ with $^{79}Br_2$, isotope pattern as calc.), 246 (14, [M—Br]⊕ with $^{79}Br$), 177 (38, [M—2Br]⊕), 150 (10), 75 (16). IR (KBr) ν=3050 cm$^-$ (w, ν[C—H]); 1620 (s, ν[C═C] ); 740 (s, γ[C—H]

H NMR (200 MHz, CDCl$_3$): δ=8.78 (s, 1H, 9-H), 8.18 (dd), 7.98 (dd), 7.40 (dd) [AMX spin system with $^3J_{MX}$=8.5 Hz, $^3J_{AX}$=7.2 Hz, $^4J_{AM}$=1.4 Hz, 2H each for 3-, 6-H (A), 1-, 8-H (M), 2-, 7-H (X)]. $^{13}$C NMR (50 MHz, CDCl$_3$): δ=145.8 (s, C-4a, -10a), 137.4 (d, C-9), 134.0 (d, C-1, -8 or C-3, -6), 127.8 (d C-1, -8 or C-3, -6), 127.5 (s, C-8a, -9a), 126.5 (d, C-2, -7), 125.7 (s, C-4, -5). Increment calculations were performed to assist the assignment.

What is claimed is:

1. A compound of the formula (II):

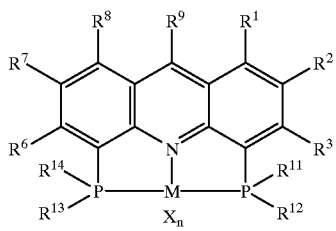

(II)

wherein $R^1$, $R^2$, $R^3$, $R^6$ $R^7$, $R^8$ and $R^9$ each represent hydrogen atoms, or at least one or two of $R^1$, $R^2$, $R^3$, $R^6$, $R^7$, $R^8$ and $R^9$ may independently represent an alkyl or alkoxy group each having from 1 to 12 carbon atoms, aryl, $NH_2$, $NR_2$, $NR_3^+Y^-$ (where $R=C_1$ to $C_4$ alkyl and $Y^-$=an anion), OH, COOH, $SO_3H$, halogen, $CF_3$, or a substituted alkyl alkoxy or aryl group;

$R^{11}$, $R^{12}$, $R^{13}$ and $R^{14}$ independently represent an aryl, aralkyl, alkaryl, alkyl or cycloalkyl group, or a substituted phenyl or alkyl group; or $R^{11}$ and $R^{12}$ together or $R^{13}$ and $R^{14}$ together may be linked to one another to form a phosphacycloalkane ring;

M represents a transition metal selected from the group consisting of Ti, V, Cr, Mn, Fe, Co, Ni, Cu, Zr, Nb, Mo, Ru, Rh, Pd, Ag, Hf, Ta, W, Re, Os, Ir, Pt and Au;

n represents, depending on the oxidation state of M, the number 0, 1, 2 or 3; and each X, when present, independently represents an anion or ligand bound to M.

2. The compound according to claim 1, wherein $R^{11}$, $R^{12}$, $R^{13}$ and $R^{14}$ are the same and are unsubstituted.

3. The compound according to claim 1, wherein $R^1$, $R^2$, $R^3$, $R^6$, $R^7$, $R^8$ and $R^9$ each represent hydrogen atoms.

4. The compound according to claim 1, wherein $R^1$, $R^2$, $R^3$, $R^6$, $R^7$, $R^8$ and $R^9$ each represent hydrogen atoms and $R^{11}$, $R^{12}$, $R^{13}$ and $R^{14}$ each independently represent an aryl, aralkyl, alkaryl, alkyl or cycloalkyl group.

5. The compound according to claim 1, wherein $R^1$, $R^2$, $R^3$, $R^6$, $R^7$, $R^8$ and $R^9$ each represent hydrogen atoms and $R^{11}$, $R^{12}$, $R^{13}$ and $R^{14}$ each represent phenyl.

6. The compound according to claim 1, wherein either $R^9$ alone or both $R^2$ and $R^7$ represent an alkyl or alkoxy group each having from 1 to 12 carbon atoms, aryl, $NH_2$, $NR_2$, $NR_3^+Y^-$ (wherein $R=C_1$ to $C_4$ alkyl and $Y^-$=a halide), OH, COOH, $SO_3H$, halogens or $CF_3$, or represent an alkyl, alkoxy or aryl group substituted with one or more groups independently selected from the group consisting of $NH_2$, $NR_2$, $NR_3^+Y^-$ (wherein $R=C_1$ to $C_4$ alkyl and Y=a halide), OH, COOH, $SO_3H$, halogens and $CF_3$; and/or $R^{11}$, $R^{12}$, $R^{13}$ and $R^{14}$ independently represent an aryl, aralkyl, alkaryl, alkyl or cycloalkyl group, or a phenyl or alkyl group substituted with one or more groups independently selected from the group consisting of $NH_2$, $NR_2$, $NR_3^+Y^-$ (wherein $R=C_1$ to $C_4$ alkyl and $Y^-$=a halide), OH, COOH, $SO_3H$, halogens or $CF_3$; and/or each X, when present, represents an anion or ligand independently selected from the group consisting of $F^-$, $Cl^-$, $Br^-$, $I^-$, cyanide, acetate, propionate, trifluoroacetate, acetylacetonate, hexafluoroacetylacetonate, sulfate, alkylsulfonate, arylsulfonate, trifluoromethanesulfonate, hydride, alkyl, aryl, carbon monoxide, nitrosyl, trialkylphosphine, triarylphosphine, trialkylphosphite triarylphosphite, ethylene, olefins, acetylenes, cyclopentadienyl and benzene.

7. A compound of the formula (I):

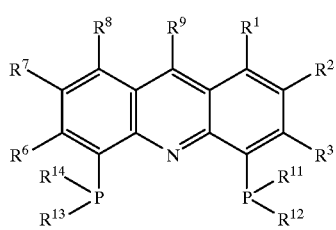

(I)

wherein $R^1$, $R^2$, $R^3$, $R^6$, $R^7$, $R^8$ and $R^9$ each represent hydrogen atoms, or at least one or two of $R^1$, $R^2$, $R^3$, $R^6$, $R^7$, $R^8$ and $R^9$ may independently represent an alkyl or alkoxy group each having from 1 to 12 carbon atoms, aryl, $NH_2$, $NR_2$, $NR_3^+Y^-$ (where $R=C_1$ to $C_4$ alkyl and $Y^-$=an anion), OH, COOH, $SO_3H$, halogen, $CF_3$, or a substituted alkyl, alkoxy or aryl group, and $R^{11}$, $R^{12}$, $R^{13}$ and $R^{14}$ independently represent an aryl., aralkyl, alkaryl, alkyl or cycloalkyl group, or a substituted phenyl or alkyl group; or $R^{11}$ and $R^{12}$ together or $R^{13}$ and $R^{14}$ together may be linked to one another to form a phosphacycloalkane ring.

8. The compound according to claim 7, wherein $R^{11}$, $R^{12}$, $R^{13}$ and $R^{14}$ are the same and are unsubstituted.

9. The compound according to claim 7, wherein $R^1$, $R^2$, $R^3$, $R^6$, $R^7$, $R^8$ and $R^9$ each represent hydrogen atoms.

10. The compound according to claim 7 wherein $R^1$, $R^2$, $R^3$, $R^6$, $R^7$, $R^8$ and $R^9$ each represent hydrogen atoms and $R^{11}$, $R^{12}$, $R^{13}$ and $R^{14}$ each independently represent an aryl, aralkyl, alkaryl, alkyl or cycloalkyl group.

11. The compound according to claim 7, wherein $R^1$, $R^2$, $R^3$, $R^6$, $R^7$, $R^8$ and $R^9$ each represent hydrogen atoms and $R^{11}$, $R^{12}$, $R^{13}$ and $R^{14}$ each represent phenyl.

12. The compound according to claim 7, wherein either $R^9$ alone or both $R^2$ and $R^7$ represent an alkyl or alkoxy group each having from 1 to 12 carbon atoms, aryl. $NH_2$, $NR_2$, $NR_3^+Y^-$ (wherein $R=C_1$ to $C_4$ allyl and $Y^-$=a halide), OH, COOH, $SO_3H$, halogens or $CF_3$, or represent an alkyl, alkoxy or aryl group substituted with one or more groups independently selected from the group consisting of $NH_2$, $NR_2$, $NR_3^+Y^-$ (wherein $R=C_1$ to $C_4$ alkyl and $Y^-$=a halide), OH, COOH, $SO_3H$, halogens and $CF_3$; and/or $R^{11}$, $R^{12}$, $R^{13}$ and $R^{14}$ independently represent an aryl, aralkyl, alkaryl, alkyl or cycloalkyl group, or a phenyl or alkyl group substituted with one or more groups independently selected from the group consisting of $NH_2$, $NR_2$, $NR_3^+Y^-$ (wherein $R=C_1$ to $C_4$ alkyl and $Y^-$=a halide), OH, COOH, $SO_3H$, halogens or $CF_3$.

13. A compound formed in situ from a mixture of a compound of the formula (I) according to any one of claims 7–12 and a transition metal compound comprising an element selected from the group consisting of Ti, V, Cr, Mn, Fe, Co, Ni, Cu, Zr, Nb, Mo, Ru, Rh, Pd. Ag, Hf, Ta, W, Re, Os, Ir, Pt and Au, said mixture containing said compound of the formula (I) and said transition metal compound in a ratio of between 0.1 and 100.

14. A compound according to claim 13, wherein said mixture contains said compound of the formula (I) and said transition metal compound in a ratio of between 0.5 and 10.

15. A composition comprising a mixture of a transition metal compound according to any one of claims 1–6 and at least one lewis acid or soluble silver (I) salt, wherein the amount of said at least one lewis acid or soluble silver (I) salt in the composition is from 1 to 10 equivalents of the transition metal compound.

16. The composition according to claim 15, wherein the lewis acid is selected from the group consisting of $AlCl_3$, $BF_3$, $SnCl_2$, $ZnCl_2$, $SbF_3$ and $SbF_5$.

17. A process for preparing a transition metal compound of the formula (II) according to claim 1, said process comprising reacting a compound of the formula (I):

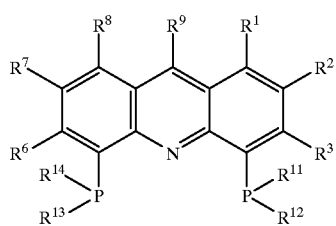

(I)

wherein $R^1$, $R^2$, $R^3$, $R^6$, $R^7$, $R^8$ and $R^9$ each represent hydrogen atoms, or at least one or two of $R^1$, $R^2$ $R^3$, $R^6$, $R^7$, $R^8$ and $R^9$ may independently represent an alkyl or alkoxy group each having from 1 to 12 carbon atoms, aryl, $NH_2$, $NR_2$, $NR_3^+Y^-$ (where $R=C_1$ to $C_4$ alkyl and $Y^-$=an anion), OH, COOH, $SO_3H$, halogen, $CF_3$, or a substituted alkyl, alkoxy or aryl group; and $R^{11}$ $R^{12}$, $R^{13}$ and $R^{14}$ independently represent an aryl, aralkyl, alkaryl, alkyl or cycloalkyl group, or a substituted phenyl or alkyl group; or $R^{11}$ and $R^{12}$ together or $R^{13}$ and $R^{14}$ together may be linked to one another to form a phosphacycloalkane ring;

with a transition metal compound comprising an element selected from the group consisting of Ti, V, Cr, Mn, Fe, Co, Ni, Cu, Zr, Nb, Mo, Ru, Rh, Pd, Ag, Hf, Ta, W, Re, Os, Ir, Pt and Au in an organic solvent at a temperature of between −100° C. and +200° C.

18. The process according to claim 17, wherein the organic solvent is selected from the group consisting of hydrocarbons, ethers, tetrahydrofuran, dimethoxyethane, 1,4-dioxan, carbon tetrachloride, chlorohydrocarbons, alcohols, acetone, acetonitrile, and dimethylformamide.

19. The process according to claim 17, wherein the organic solvent is selected from the group consisting of benzene, toluene, diethyl ether, tetrahydrofuran, dimethoxyethane, 1,4-dioxan, carbon tetrachloride, dichloromethane, chloroform, butanol, acetone, acetonitrile, and dimethylformamide.

20. The process according to any one of claims 17–19, which is carried out at a temperature of between 0° C. and 100° C.

21. A process comprising conducting a chemical reaction in the presence of a catalyst thereof, wherein said catalyst is a compound according to any one of claims 1–6.

22. The process according to claim 21, wherein the chemical reaction is selected from the group consisting of carbon monoxide conversion via a water-gas shift reaction, which proceeds according to the scheme: $CO+H_2O \rightarrow CO_2+H_2$, hydroformylation, carbonylation, carboxylation, hydrogenation. hydrocyanogenation, hydrosilylation polymerization, isomerization, cross-couplings and metathesis.

23. The process according to claim 22, which comprises reacting solid, liquid or gaseous reactants in the presence of said catalyst dissolved in an organic solvent, water or a mixture ol different solvents with or without water at a temperature of between −100° C. and +300° C. and a pressure of between 1 bar and 300 bar.

24. The process according to claim 23, which comprises reacting solid, liquid or gaseous reactants in the presence of said catalyst dissolved in an organic solvent, water or a mixture of different solvents with or without water at a temperature of between 0° C. and 200° C. and a pressure of between 1 bar and 100 bar.

25. The process according to claim 21, wherein the chemical reaction produces hydrogen from carbon monoxide and water via a water-gas shift reaction, which proceeds according to the reaction scheme: $CO+H_2O \rightarrow CO_2+H_2$, and comprises reacting carbon monoxide or gases containing carbon monoxide with water in the presence of said catalyst, optionally using a water-miscible organic solvent, and at a temperature of between 0° C. and 300° C. and a pressure of between 1 bar and 300 bar.

26. The process according to claim 25, which comprises reacting carbon monoxide or gases containing carbon monoxide with water in the presence of said catalyst, optionally using a water-miscible organic solvent selected from the group consisting of alcohols, tetrahydrofuran, dimethoxyethane, 1,4-dioxan, glycol, glycol dialkyl ether, and oligomeric glycols or their dialkyl ethers, and/or at a temperature of between 100° C. and 250° C. and a pressure of between 1 bar and 100 bar.

27. The process according to claim 15, wherein the catalyst is 4,5-bis(diphenyl-phosphino) acridinepalladium (II) chloride (VIII).

28. The process according to claim 26, wherein the catalyst is 4,5-bis(diphenyl-phosphino) acridinepalladium (II) chloride (VIII).

29. A process for preparing a compound of the formula (I) according to claim 7, said process comprising reacting a 4.5-dihaloacridine of the formula:

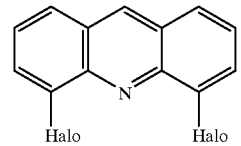

wherein

Halo represents F, Cl, Br or I:

with an alkali metal phosphide in an aprotic organic solvent at a temperature of between −100° C. and +200° C.

30. The process according to claim 29, wherein the dihaloacridine is 4,5-difluoroacridine (XIII), and/or the alkali metal phosphide has the formula $R_2P^-M^{1+}$, wherein R=alkyl, phenyl or aryl, and $M^{1+}=Li^+$, $Na^+$, $K^+$, $Rb^+$ or $Cs^+$; and/or the aprotic organic solvent is selected from the group consisting of hydrocarbons, ethers, tetrahydrofuran, dimethoxyethane, 1,4-dioxan, oligomeric ethylene glycol dimethyl ethers. hexamethylphosphoric triamide, and N-methyl-2-pyrrolidinone; and/or the temperature is between 0° C. and +150° C.

31. The process according to claim 30, wherein the dihaloacridine is 4,5-difluoroacridine (XIII); and/or the alkali metal phosphide is an alkali metal diphenylphosphide of the formula $Ph_2P^-M^{1+}$, wherein $M^{1+}=Li^+$, $Na^+$, $K^+$, $Rb^+$ or $Cs^+$; and/or the aprotic organic solvent is selected from the group consisting of hydrocarbons, ethers, tetrahydrofuran, dimethoxyethane, 1,4-dioxan, oligomeric ethylene glycol dimethyl ethers, hexamethylphosphoric triamide, and N-methyl-2-pyrrolidinone; and/or the temperature is between 0° C. and +150° C.

32. The process according to any one of claims 29–31, wherein the dihaloacridine is 4,5-difluoroacridine (XIII); and/or the alkali metal phosphide is potassium diphenylphosphide; and/or the aprotic organic solvent is 1,4-dioxan; and/or the temperature is between 0° C. and +150° C.

33. A process for preparing a compound of the formula (I) according to claim 7, said process comprising reacting a 4,5-dihaloacridine of the formula:

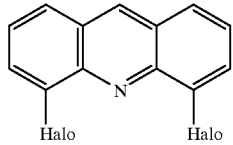

wherein

Halo represents Fe Cl, Br or I;

with a chlorophosphine and magnesium in an aprotic organic solvent at a temperature of between −100° C. and +100° C.

34. The process according to claim 33, wherein the dihaloacridine is 4,5-dibromnoacridine (XIX); and/or the chlorophosphine has the formula $R_2PCl$, wherein R=alkyl, phenyl or aryl; and/or the aprotic organic solvent is selected from the group consisting of hydrocarbons, ethers, tetrahydrofuran, dimethoxyethane, 1,4-dioxan, oligomeric ethylene glycol dimethyl ethers, hexamethylphosphoric triamide, and N-methyl-2-pyrrolidinone; and/or the temperature is between 0° C. and +100° C.

35. The process according to claim 34, wherein the dihaloacridine is 4,5-dibromoacridine (XIX); and/or the chlorophosphine is chlorodiphenylphosphine; and/or the aprotic organic solvent is selected from the group consisting of hydrocarbons, ethers, tetrahydrofuran, dimethoxyethane 1,4-dioxan, oligomeric ethylene glycol dimethyl ethers, hexamethylphosphoric triamide, and N-methyl-2-pyrrolidinone; and/or the temperature is between 0° C. and +100° C.

36. The process according to any one of claims 33–35, wherein the dihaloacridine is 4.5-dibromoacridine (XIX); and/or the chlorophosphine is chlorodiphenylphosphine; and/or the aprotic organic solvent is tetrahydrofuran; and/or the temperature is between 0° C. and +100° C.

* * * * *